United States Patent [19]

Bollyky

[11] 3,970,660

[45] July 20, 1976

[54] CHEMILUMINESCENCE

[75] Inventor: Laszlo Joseph Bollyky, Stamford, Conn.

[73] Assignee: American Cyanamid Company, Stamford, Conn.

[22] Filed: July 22, 1974

[21] Appl. No.: 490,427

Related U.S. Application Data

[60] Continuation of Ser. No. 211,807, Dec. 23, 1971, abandoned, which is a division of Ser. No. 844,657, July 24, 1969, abandoned, which is a continuation-in-part of Ser. No. 547,782, May 5, 1966, abandoned.

[52] U.S. Cl. .................... 260/295 L; 252/188.3 CL; 252/301.16; 260/248 NS; 260/276; 260/295 R; 260/289 R; 260/302 A; 260/306.8 R; 260/307 A; 260/307 G; 260/308 R; 260/309; 260/326 A; 260/397.7 R; 260/465 E; 260/556 B; 260/556 AR; 260/577

[51] Int. Cl.$^2$........................................ C07D 211/86

[58] Field of Search..... 260/295 AM, 295 L, 296 O; 252/188.3 CL

[56] References Cited
OTHER PUBLICATIONS

Gavrilov et al., Chemical Abstracts, vol. 43, cols. 3789 to 3790 (1949).

Schotten, Ber. Deut. Chem. vol. 15, pp. 421 to 427 (1882).

Beilstein's Handbuch der Organischen Chemie, 4th Ed. vol. 20, p. 48, system no. 3038, Von Julius Springer, Berlin Germany (1935).

Sebenda et al., Chemical Abstracts, vol. 55, col. 17084 (1961) (abst. of Czech pat. 93,016).

Gleu et al., Chem. Ber. vol. 72, pp. 1093 to 1099 (1939).

Chem. Abstracts, vol. 44, cols. 6417 to 6418 (1950) (abst. of Gautier et al.).

Chem. Abstracts, vol. 42, col. 3754 (1942) (abst. of Gautier et al.).

*Primary Examiner*—John D. Randolph
*Attorney, Agent, or Firm*—Charles J. Fickey; Gordon L. Hart

[57] ABSTRACT

A chemiluminescent system comprising (1) derivatives of a polycarbonyl compound substituted with at least one nitrogen-containing hetero group and which may have an alkanol or amine substituent, (2) a hydroperoxide compound, (3) a diluent, and (4) a fluorescer, said ingredients in combination producing visible chemiluminescent light and a process of producing such light.

1 Claim, No Drawings

CHEMILUMINESCENCE

This application is a continuation of Ser. No. 211,807, filed Dec. 23, 1971 and now abandoned, which application was a division of Ser. No. 844,657 filed July 24, 1969, now abandoned, which application was in turn a continuation-in-part of Ser. No. 547,782 filed May 5, 1966, now abandoned.

The present invention relates to novel polycarbonyl compounds which obtain chemiluminescent light when reacted with other necessary chemiluminescent reactants in the direct generation of light from chemical energy. By "light" as referred to herein is meant electromagnetic radiation at wavelengths falling between about 350 m$\mu$ and about 800 m$\mu$.

The art of generating light from chemical energy, i.e. chemiluminescence, is continually in search of compositions which when reacted substantially improve the intensity and lifetime of light emission contrasted to known chemiluminescent compositions and reactions. Obviously, improved compositions are constantly in demand for use as signal devices, for area illumination, etc.

It is an object of this invention to obtain a chemiluminescent composition and a process employing said composition whereby a high efficiency may be obtained in the conversion of chemical energy into light.

Another object is to obtain a chemiluminescent compound which produces light over an extended period of time.

Another object of this invention is to obtain a chemiluminescent composition which attains light of substantially higher intensity and with a greater degree of quantum efficiency than has been obtained with former chemiluminescent compositions.

Another object of this invention is to obtain a chemiluminescent composition which may be employed to obtain light by a process which is mechanically simple and which is economically inexpensive.

Another object of this invention is to obtain a chemiluminescent reactant which is stable over a long period of time and wich may be subsequently reacted to obtain chemiluminescent light.

Another object of this invention is to obtain a chemiluminescent reactant which when reacted will obtain chemiluminescent light by a process which is not hazardous.

Another object is to obtain a composition characterized by its ability to undergo partial chemiluminescence, followed by reversal to a substantially non-chemiluminescent state.

Another object is to obtain a composition characterized by a controllable (1) length of duration of chemiluminescence and (2) intensity of chemiluminescent illumination.

Another object is to obtain a process of regulating intensity and duration of chemiluminescence.

Other objects of this invention become apparent from the above and following disclosure.

The term "tautomerism" as used herein means the coexistence of two or more compounds that differ from each other only in the position of one or more mobile atoms and in electron distribution, a typical illustrating example of tautomeric forms being:

The term "rearrangement" as used herein means the conversion of a compound to one or more different compounds that differ from each other, and from the starting compound in the position of one or more mobile atoms and in electron distribution. The term rearrangement also includes any subsequent or concurrent conversion of the compounds involved in a rearrangement (as defined above) to their conjugate acid or base or a salt of the conjugate acid or base.

The term "aromatic compound" as used herein includes both benzenoid compounds and heterocyclic compounds which are characterized by substantial resonance energy ( >5 kcal per mole) and by the tendency to undergo substitution reactions with reagents that ordinarily add to a double bond. Accordingly, monocyclic, polycyclic, and heterocyclic compounds are also included.

The term "aryl group" as used herein means a group which is derived from an aromatic compound by the removal of one or more atoms.

The term "chemiluminescent reactant", as used herein, means (1) a mixture which will result in a chemiluminescent reaction when reacted with other necessary reactants in the processes as disclosed herein, or (2) a chemiluminescent composition.

The term "fluorescent compound", as used herein, means a compound which fluoresces in a chemiluminescent reaction, or a compound which produces a fluorescent compound in a chemiluminescent reaction.

The term "chemiluminescent composition", as used herein, means a mixture which will result in chemiluminescence.

The term "admixing", as used herein, means "reacting" or sufficiently bringing together component reactants to obtain a chemiluminescent reaction.

The term "hydroperoxide compound" as used herein is limited to peroxide compounds having at least one HOO— group, or a compound which upon reaction produces a compound with such a group.

The term "peroxidic groups", as used herein, represents "HOO—", "ROO—", or

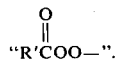

"R'" is defined for the polycarbonyl compound below, while R is a substituent such as alkyl, cycloalkyl, $\alpha$-hydroxyalkyl, substituted alkyl, for example.

The term "diluent", as used herein, means a solvent or a vehicle which when employed with a solvent does not cause insolubility.

The term "peroxide compound", as used herein, also includes compounds which upon reaction produce the peroxide group.

The term "hydrogen peroxide compound" includes (1) hydrogen peroxide and (2) hydrogen peroxide-producing compounds.

The objects of this invention are obtained by the employment, with other necessary chemiluminescent reactants, of a composition of the formula:

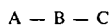

in which $B$ is a polycarbonyl group which has a substituent of each of $A$ and $C$, $B$ being of the formula:

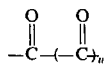

where $n$ is an integer of at least one, in which $A$ is a $Q'$hydro-$Q^2$ oxo-substituted nitrogen-containing aromatic compound onto which one terminal carbonyl group of said $B$ is substituted at a nitrogen atom of said $A$ is a $Q'$hydro-$Q^2$ oxo-substituted nitrogen-containing aromatic compound in which each of $Q'$ and $Q^2$ is a group occurring at least once and the value of $Q'$ is greater than, and preferably twice the value of $Q^2$, in which $Q'$ describes the number of hydro substituents present on the aromatic groups, and $Q^2$ describes the number of oxo substituents present on the aromatic group, said $A$ being represented by the structure:

said $Q'$ and $Q^2$ being as above recited, and

representing a mono- or polycyclic nitrogen-containing heterocyclic group, $m$ and $p$ being integers of at least one, $m$ being greater than $p$, and $m$ preferably being at least twice $p$, and in which said $C$ is a compound selected from the group consisting of (1) said $A$, (2) an alcohol of the formula $R' - O - H$ forming an ester of a carbonyl group of said $B$, in which $R'$ is selected from the group consisting of (a) aryl, (b) electronegatively substituted alkyl, (c) heterocyclicalkylaryl, and (d) unsaturated alkyl, and (3) an amine which forms an amide with a terminal carbonyl group of said $B$ and which amine is selected from the group consisting of:

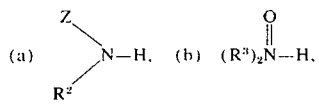

(c) $R^4—N=N—H$, and (d) strongly electronegatively N-substituted (substituted or non-substituted) nitrogen-containing heterocyclic compounds, where the N- is attached directly to a terminal carbonyl carbon of said B, typical N-substituted nitrogen-containing heterocyclic compounds including compounds of the formula:

where any one or more of the heterocyclic compounds may include alkyl substituents and typical electronegative substituents such as above $a$ through $e$ including cyano, halogen, sulfo, oxygen-substituted phosphorous substituents, etc.; where $R^4$ is selected from the group consisting of hydrogen and the members of $R^3$, where $R^3$ is selected from the group consisting of alkyl, aryl, cycloalkyl, heterocyclic, polycyclic, amino, and alkyl- or aryl or acyl-substituted amino substituents; where $R^2$ is selected from the group consisting of the members of both $R^4$ and the following electronegatively substituted groups: (a) mono, poly-, and aryl groups substituted further by at least one electronegative group, where the electronegative substituent of said aryl group is typically a member selected from the groups consisting of (I) nitro, (II) a halogen, provided at least three halogen substituents are present in the amide, (III) oxygenated-sulfur substituents such as

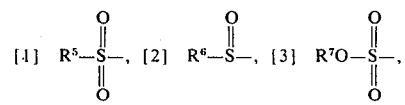

and

where $R^5$ and $R^6$ are each selected from the group consisting of alkyl, aryl, cycloalkyl, heterocyclic, and polycyclic substituents, and where $R^7$ and $R^9$ are each selected from the group consisting of hydrogen and the members of $R^5$ defined above, (IV) cyano, (V) a polyfluoroalkyl substituent such as $F_3C—$, $F_5C_2—$, $F_3H_2C_2—$, $F_2CH—$, and $F_2C_2H_2(CH_3)—$, $F_3C_2H_2—$, $F_2C_3H_5—$, etc. and (VI) an acyl substituent of the formula

where $R^9$ is defined the same as $R^7$, provided that said aryl group includes a sufficient number of electronegative members to obtain an acidity of the amine at least as great as the acidity of 4-nitroaniline, (b) a polyfluoroalkyl substituent as defined above, and (c) an acyl substituent as defined above; where Z is a member selected from the group consisting of (a) cyano (i.e., NC—), (b) nitrosyl (ON—), (c) nitroxyl ($O_2N$—), (d) oxygenated-sulfur substituents such as

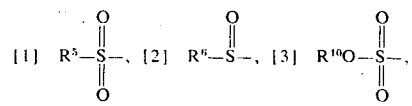

and

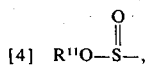

where $R^5$, $R^6$ are defined above and $R^{10}$ and $R^{11}$ are each defined the same as $R^5$, and (e) oxygen-substituted phosphorous substituents such as $(R^{12})_2P-$, and $(R^{13}O)_2P-$, where $R^{12}$ and $R^{13}$ are defined the same as $R^4$.

In the preferred embodiment C is the same as A, thereby forming the preferred symmetric polycarbonyl compound.

In the preferred embodiment of the generic formula, the compounds which obtain optimum chemiluminescence when reacted are characterized by a rearrangement to an ester which is more reactive and produces chemiluminescence more efficiently.

In a preferred embodiment of the generic formula, $n$ ranges from about 1 to about 4.

We have unexpectedly discovered that the objects of this invention are obtained by the preparation of any one of the above generic compounds, and subsequently admixing the above generic compound of this invention with other necessary reactants to obtain chemiluminescence, the other reactants including at least one of each of hydroperoxide, a diluent, and a fluorescer (fluorescent compound). Moreover, unexpectedly superior results are obtained by including at least sufficient acidic material to obtain an acid pH, whereby a more intense chemiluminescent light is obtained substantially proportional to the increased acidity of the reaction mixture. Also it was unexpectedly discovered that light intensity may be substantially quenched or "suspended" by the addition of alkaline material to the acidic mixture. It is also unexpectedly discovered that light intensity and the quantum efficiency may be substantially increased by increasing the concentration of the generic compound (of this invention) in the reaction mixture. An increase in the concentration of the generic compound and/or a lowering of the pH, in the reaction mixture, obtains a substantially increased intensity of chemiluminescent light. If solely the pH of the reaction mixture is lowered, the lifetime of the chemiluminescent reaction will be shortened. The addition of an alkaline material to an acidic reaction mixture retards the rate of reaction presumably by retarding or preventing rearrangement of the remaining stable polycarbonyl compound and thereby increase the duration of time during which chemiluminescence may be obtained. Subsequent addition of acid material to an alkaline media increases the rate of reaction. Depending upon the combination of variable factors as discussed above, the intensity or reaction and the rate of reaction may be extended over a period of 12 hours or more.

In the preferred embodiment, bis(1,2-dihydro-2-oxo-1-pyridyl)glyoxal is employed, and is reacted in the presence of an acidic material, where the reaction media includes also a hydroperoxide and a fluorescer.

In any of the embodiments of this invention, as shall be further discussed below, the fluorescer or the hydroperoxide may each or both be intimate parts of other reactant molecules. A typical example is a situation in which the fluorescent material is an intimate part of the bis($Q'$hydro-$Q^2$ oxo substituted-nitrogen-aryl)polycarbonyl molecule.

Typical $Q'$hydro-$Q^2$ oxo substituted nitrogen containing aromatic compounds comprise: (I) compounds that contain at least one nitrogen as a hetero atom such as 1,2-dihydro-2-oxopyridine or 2-hydroxy-pyridine the tautomeric form.

A typical compound of this invention in which A and C are each a derivative of the tautomeric compound symmetric-1,2-dihydro-2-oxopyridine and $n$ is 1, is represented by the formula:

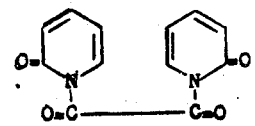

Rearrangement in the presence of an acid HX (acid) may result in the formation of one or more of the following compounds:

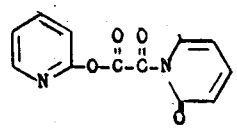 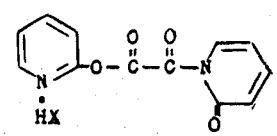

or

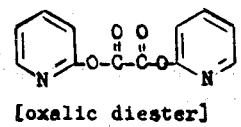

[oxalic diester]

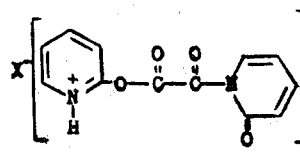

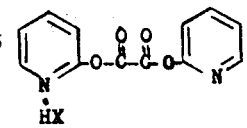 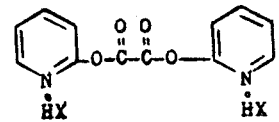

However, the invention disclosed herein is not to be restricted to this theory, except as limited in the appended claims.

Other examples of the A (as defined above) are $Q'$hydro-$Q^2$ oxo substituted nitrogen containing aromatic compounds as follows:

(1) compounds that contain one oxo substituent as: e.g., 1,2-dihydro-2-oxoquinoline, 1,5-dihydro-5-oxoquinoline, 2,3-dihydro-3-oxoisoquinoline, etc. and

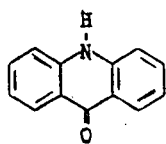

9,10-dihydro-9-oxoacridine (i.e. acridone);

(2) compounds that contain more than one oxo-substituent as: e.g., 1,2,3,4-tetrahydro-2,4-dioxopyridine, hexahydro-2,4,6-trioxopyridine, 1,2,3,4-tetrahydro-2,4-dioxoquinoline.

Other typical Q'hydro-Q² oxo substituted nitrogen containing aromatic compounds that contain at least one nitrogen and at least another heteroatom than nitrogen, include:

1. compounds that contain one oxo substituent as: e.g., 2,3-dihydro-3-oxoisothiazole, 2,3-dihydro-2-oxooxazole,
2. compounds that contain more than one oxo substituent e.g., 2,3,4,5-tetrahydro-3,4-dioxoisoxazole.

Typical Q'hydro-Q² oxo substituted nitrogen containing aromatic compounds that contain more than one nitrogen heteroatom include:

1. compounds that contain more than one nitrogen heteroatom but which:
   a. contain only one oxo substituent e.g., 1,2-dihydro-2-oxo-1,3,5-triazine, 1,6-dihydro-6-oxopentazine,
   b. contain more than one oxo substituent e.g., hexahydro-2,4,6-trioxo-1,3,5-triazine;
2. compounds than contain more than one nitrogen heteroatom and at least another heteroatom other than nitrogen but which:
   a. contain only one oxo substituent e.g., 2,3-dihydro-3-oxofurazan, 4,5-dihydro-5-oxo-1,2,3,4-oxatriazole,
   b. contain more than one oxo substituent e.g., tetrahydro-2,5-dioxo-1,3,4-oxadiazole, tetrahydro-3,4-dioxofurazan.

All the typical Q'hydro-Q² oxo substituted nitrogen containing aromatic compounds described above may be substituted further by alkyl aryl and cyclic alkyl groups and by groups such as R', R², R³ and R⁴, already defined above.

In the typical formula described above, the C may also represent any one of the following group of compounds: (1) an alcohol of the following typical formula:

R' — O — H where R represents:

A. electronegatively substituted alkyl groups such as those substituted at the α or β positions by:
   a. by halogen: e.g., trifluoromethyl-, trichloromethyl-, perfluoroethyl-, perfluorodecyl-, 1,1,2,2-tetrafluorocyclohexyl-.
   b. by carboxy groups: e.g., carboxymethyl-, carboxyethyl-;
   c. by heterocyclic groups: e.g., pyridylethyl-, furylmethyl-, tetrahydrofurylpropyl-, acridinylethyl-;
   d. by sulfo groups: e.g., sulfomethyl-;
B. aryl groups: e.g., phenyl-, naphthyl-, or substituted aryl groups by typical substituents such as:
   a. by halogen: e.g., pentafluorophenyl-, dichlorophenyl-, dibromophenyl-;
   b. by acyloxy groups: e.g., benzoyloxyphenyl-;
   c. by carbonyl groups: e.g., formylphenyl-, acetylphenyl-;
   d. by carboxyl groups: e.g., carboxyphenyl-;
   e. by nitro groups: e.g., 2,4-dinitrophenyl-, 4-nitrophenyl-;
   f. by heterocyclic groups: e.g., pyridylphenyl-, tetrahydrofurylphenyl-;
   g. by sulfo groups: e.g., 2-nitro-4-sulfophenyl-, 2-nitro-4-sulfonaphthyl-;
   h. by cyano groups: e.g., 4-cyanophenyl-;
C. heterocyclic groups: e.g., pyridyl-, furyl-, acridinyl-, or substituted heterocyclic groups by typical substituents such as:
   a. by alkyl groups: e.g., methylpyridyl-;
   b. by halogen: e.g., chloropyridyl-;
   c. by acyloxy groups: e.g., acetoxypyridyl-;
   d. by carbonyl groups: e.g., formylpyridyl-;
   e. by carbonyl groups: e.g., carboxypyridyl-;
   f. by alkoxy groups: e.g., methoxyfuryl-;
   g. by amino groups: e.g., dimethylaminotetrahydrofuryl-;
   h. by sulfo groups: e.g., sulfofuryl-;
   i. by hydroxy groups: e.g., 2-hydroxypyridyl-;
D. unsaturated alkyl and cyclic alkyl groups: e.g., vinyl-, allyl, ethynyl-, cyclohexenyl-, isopropenyl-.

As stated above, C may be an amine. Typical illustrative amines are as follows:

a)

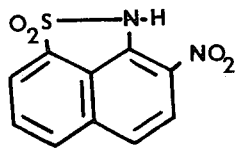

7-nitro-1,8-naphthosultam b)

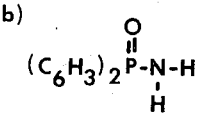

(diphenylphosphinyl)amine c)

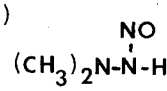

(dimethylamino)nitrosoamine d) 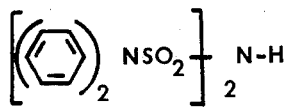 bis(diphenylsulfamoyl)amine e) 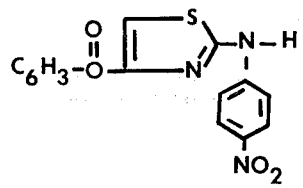 (4-benzoyl-2-thiazolyl)(p-nitrophenyl)amine f) 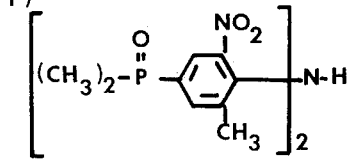 bis[4-(dimethylphosphinyl)-6-nitro-o-tolyl]amine g) 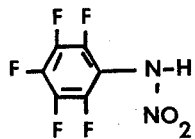 nitro(pentafluorophenyl)amine h) 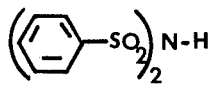 bis(phenylsulfonyl)amine i) 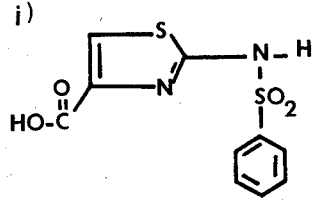 (4-carboxy-2-thiazolyl)(phenylsulfonyl)amine k) 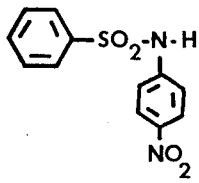 (p-nitrophenyl)(phenylsulfonyl)amine l) 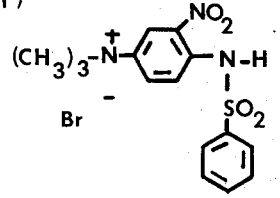 [2-nitro-4-(N-bromo-N,N,N-trimethylammonio)phenyl](phenylsulfonyl)amine m) 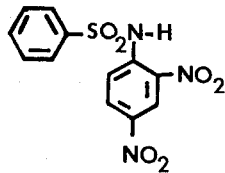 (2,4-dinitrophenyl)(phenylsulfonyl)amine n) 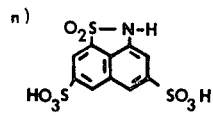 3,6-disulfo-1,8-naphthosultam o) 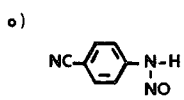 (p-cyanophenyl)nitrosoamine p) 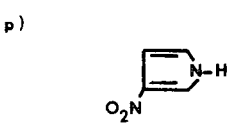 3-nitropyrrole q) 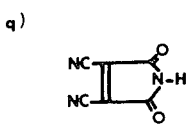 2,3-dicyanomaleimide r) 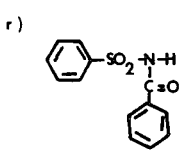 (phenylsulfonyl)benzoylamine s) 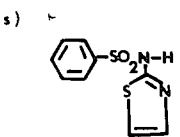 (phenylsulfonyl)2-thiazolyl)amine t) 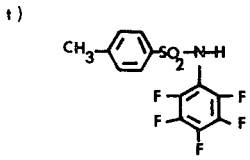 (pentafluorophenyl)(p-tolylsulfonyl)amine u) 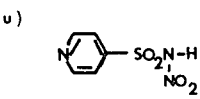 nitro(4-pyridylsulfonyl)amine v) 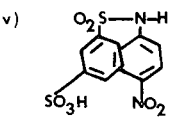 4-nitro-6-sulfo-1,8-naphthosultam w) 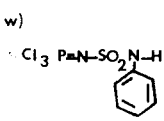 (trichlorophosphoranylidenesulfamoyl)phenylamine x)  [tri(diphenylamino)phosphoranylidenesulfamoyl]methylamine y) 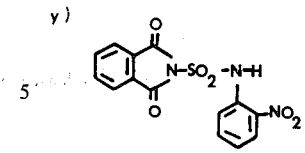 (o-nitrophenyl)(phthalimidosulfonyl)amine z) 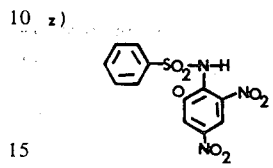 (2,4-dinitrophenyl)(phenylsulfonyl)amine aa) 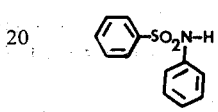 phenyl(phenylsulfonyl)amine bb) 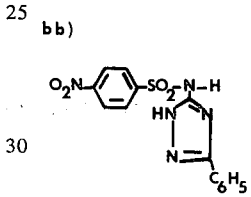 (p-nitrophenylsulfonyl)(3-phenyl-1H-1,2,4-triazol-5-yl)amino cc) 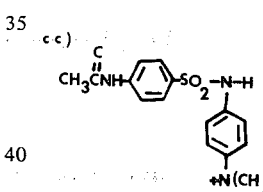 (p-acetamidophenylsulfonyl)[p-(N-bromo-N,N,N-trimethylammonio)phenyl]amine The preferred compounds of the generic formula described above within the scope of Applicant's invention include a large number of polycarbonyl compounds of the glyoxal-type which may contain two carbonyl groups. Such compounds may be typically represented by the following formula:

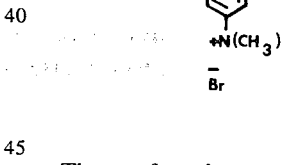

in which A and C are each defined as described above, and in which at least one hetero atom of A is a nitrogen, provided that said A is characterized by a potential rearrangement to form a heteroaromatic oxalic type ester upon reaction with other necessary chemiluminescent reactants discussed above; however, it should be noted that both in the generic (A—B—C) compounds of this invention and in the preferred polyoxal embodiments, more than one heteroatom may be present in each of A and C, and the additional heteroatom may be sulfur, phosphorous, etc.

Representative (but not exclusive) compounds falling within the above formula include:

(a) 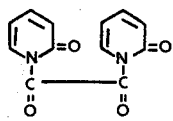 bis (1,2-dihydro-2-oxo-1-pyridyl)glyoxal, which may be written as 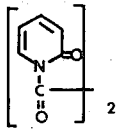

(b) 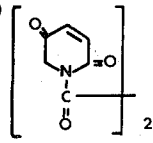 bis(1,2,5,6-tetrahydro-2,5-dioxo-1-pyridyl)glyoxal (d) 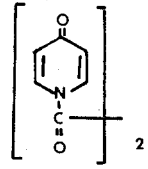
bis(1,4-dihydro-4-oxo-1-pyridyl)glyoxal ;

(e) 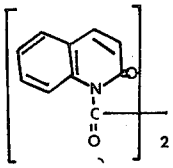
bis(1,2-dihydro-2-oxo-1-quinolyl)glyoxal ;

(f) 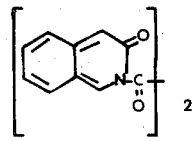
bis(2,3-dihydro-3-oxo-2-isoquinolyl)glyoxal ;

(g) 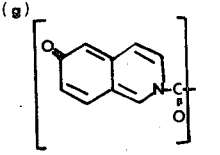
bis(2,6-dihydro-6-oxo-2-isoquinolyl)glyoxal ;

(h) 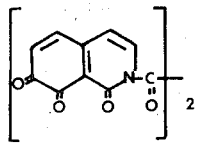
bis(1,2,7,8-tetrahydro-1,7,8-trioxo-2-isoquinolyl)glyoxal;

(i) 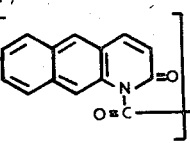
bis(1,2-dihydro-2-oxo-1-benzo[g]quinolyl)glyoxal (j) 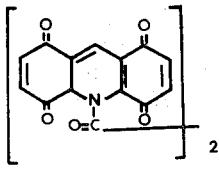
bis(1,4,5,8,10,10a-hexahydro-1,4,5 8-tetetraoxo-10-acridinyl)

(k) 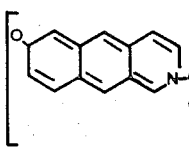
bis(2,7-dihydro-7-oxo-2-benzo[2]isoquinolyl)glyoxal

The hydroperoxide employed in the compositions and process of this invention may be obtained from any suitable peroxide compound. For example, the hydroperoxide may be employed as sodium peroxide. Alternatively, sodium perborate may be places in aqueous solution whereby a solution of hydrogen peroxide is obtained. Obviously, hydrogen peroxide or its solution may be employed. The peroxide employed may be obtained from anhydrous hydrogen peroxide compounds such as perhydrate of urea (urea peroxide), perhydrate of pyrophosphate (sodium pyrophosphate peroxide), perhydrate of histidine (histidine peroxide), sodium perborate, and the like. Still another form in which the $H_2O_2$ may be provided in the composition is that of an anhydrous solution of $H_2O_2$ in a suitable solvent such as an ether, an ester, an aromatic hydrocarbon, etc. of the type which would provide a suitable diluent for the composition of this invention. Alternatively, the hydroperoxide employed in the composition or process could be any compound having a hydroperoxidic group, such as hydroperoxide (ROOH) or a peroxy acid

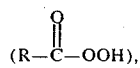

(R—C—OOH), such as t-butyl hydroperoxide and perbenzoic acid. Whenever hydrogen peroxide is contemplated to be employed, any suitable compound may be substituted which will produce hydrogen peroxide.

The hydroperoxide concentration may range from about 15 molar down to about $10^{-5}$, preferably about 2 molar down to about $10^{-4}$ molar. The generic compound of this invention may be added as a solid or in admixture with a suitable solid peroxide reactant or in a suitable diluent, or alternatively dissolved directly in a solution containing the peroxide reactant.

Typical diluents within the purview of the instant discovery are those that do not readily react with a peroxide, such as hydrogen peroxide, and which do not readily react with the polycarbonyl compound or with the rearranged polycarbonyl compound.

Although the addition of water tends to quench the production of chemiluminescent light according to the present invention, water can serve as a partial diluent up to substantial major percentages (more than 50%). The term "water", as used herein, includes water-producing compounds such as hydrates.

Any one or more suitable diluents may be included with or in the place of the water, as long as the peroxide employed is at least partially soluble in one or more of the diluent(s), such as, for example, at least one gram of $H_2O_2$ per liter of diluent. The following are typical illustrative examples of the diluents or solvents which may be singly or jointly employed: non-cyclic or cyclic ethers, such as diethyl ether, diamyl ether, diphenyl ether, anisole, tetrahydrofuran, dioxane, and the like; esters such as ethyl acetate, propyl formate, amyl acetate, dimethyl phthalate, diethyl phthalate, methyl benzoate, and the like; aromatic hydrocarbons, such as benzene, xylene, toluene, and the like, acids such as acetic or propionic acids.

The fluorescent compounds contemplated herein are numerous; and they may be defined broadly as those which do not readily react on contact with the peroxide employed in this invention, such as hydrogen peroxide; likewise, they do not readily react on contact with the generic compound of this invention. Typical suitable fluorescent compounds for use in the present invention are those which have a spectral emission falling between 330 millimicrons and 800 millimicrons and which are at least partially soluble in any of the above diluents, if such diluent is employed. Among these are the conjugated polycyclic aromatic compounds having at least 3 fused rings, such as: anthracene, substituted anthracene, benzanthracene, phenanthracene, substituted phenanthracene, naphthancene, substituted naphthacene, pentacene, substituted pentacene, and the like. Typical substituents for all of these are phenyl, lower alkyl, chlorine, bromine, cyano, alkoxy ($C_1-C_{16}$), and other like substituents which do not interfere with the light-generating reaction contemplated herein.

Numerous other fluorescent compounds having the properties given hereinabove are well known in the art. Many of these are fully described in "Fluorescence and Phosphorescence", by Peter Pringsheim, Interscience Publishers, Inc. New York, N.Y., 1949. Other fluorescers are described in "The Colour Index", Second Edition, Volume 2, The American Association of Textile Chemists and Colorists, 1956, pp. 2907–2923. While only typical fluorescent compounds are listed hereinabove, the person skilled in the art is fully aware of the fact that this invention is not so restricted and that numerous other fluorescent compounds having similar properties are contemplated for use herein.

It should be noted, however, that although a fluorescent compound is necessary to obtain the production of light, the fluorescent compound is not necessary to obtain a chemical reaction and chemical energy release. Also, a fluorescent generic compound of this invention, such as bis(9,10-dihydro-9-oxo-10-acridinyl)glyoxal does not require a separate fluorescent compound to obtain light. Other typical fluorescent, generic compounds include esters which form when C is of the generic formula one of the following alcohols: (1) 2-carboxyphenol, (2) 2-carboxy-6-hydroxyphenol, (3) 1,4-dihydroxy-9,10-diphenylanthracene, and (4) 2-naphthol. Thus, a reactant including a fluorescent generic compound of this invention would thereby include at least one fluorescent compound.

It has been found that the molar (moles per liter of diluent) concentrations of the major components of the novel composition herein described may very considerably. It is only necessary that components be in sufficient concentration to obtain chemiluminescence. The bis(dihydrooxosubstituted-hetero-heteroaromatic)-polyoxal molar concentration normally is in the range of at least about $10^{-7}$ molar, preferably in the range of at least about $10^{-4}$ to about 5 molar; the fluorescent compound is present in the range from about $10^{-5}$ to about 5, preferably about $10^{-4}$ to about $10^{-1}$ molar; and the ether or other diluent must be present in a sufficient amount to form at least a partial solution of the reactants involved in the chemiluminescent reaction. There is no known maximum limit on the concentration of the generic compound of this invention which may be employed in the reaction, and as discussed above, intense chemiluminescent light may be obtained by employment of the high concentrations.

The ingredients of the composition of this invention, may be admixed in a single stage of admixing or in a sequence of steps of admixing ingredients together or separately. Accordingly, alternative compositions may be prepared which may be stored over a period of time and which may be admixed with the final ingredient at a time when the chemiluminescent lighting is desired. For example, one such composition would be a composition which includes a generic compound of this invention and a fluorescent compound but which does not include a peroxide compound. Another alternative solid composition would be a composition which includes a peroxide, but which does not include the fluorescent compound. Another alternative composition would be a solid composition which includes a solid generic compound of this invention and a solid hydroperoxide compound, and which possibly additionally includes a solid fluorescent compound, but which does set include a diluent. Obviously, the preferred compositions which would be less than all necessary components to produce a chemiluminescent light would be a composition which would be substantially stable to a practical degree over an extended period of time; otherwise, there would be no real advantage in forming a chemiluminescent reactant to be employed in a subsequent chemiluminescent reaction.

The wavelength of the light emitted by chemiluminescence of the compositions of this invention, i.e., the color of the light emitted, may be varied by the addition of any one or more energy transfer agents (fluorescers) such as the known fluorescent compounds discussed at length above.

The wavelength of the light emitted by the composition of this invention will vary, depending upon the particular fluorescent component employed in the reaction.

Although in the process of obtaining chemiluminescent light according to this invention, it is normally not necessary to employ a specific order of sequence of steps in the adding of the individual ingredients of the inventive chemiluminescent composition, it has been found that tbe fluorescent component preferably should be already in the reaction mixture at the time of addition of the last component necessary to bring about the chemical reaction and the concurrent release of chemical energy.

Additionally, it has been found that the superior intensity of chemiluminescence is obtained when the final mixture producing the luminescence is maintained at a temperature of between about $-40°$ and $100°C$., preferably between about $20°$ and $50°C$; the luminescence of Applicant's process is not limited to these ranges and temperature is not critical.

Additionally, the composition and the process which obtains preferred optimum chemiluminescent light intensity employs an acid in an amount sufficient to produce an acidic pH. However, the preferred extended lifetime is obtained under about neutral conditions. Any suitable acid which does not interfere with the chemiluminescent combination and process of this invention may be employed.

The preferred composition and the preferred process which obtains chemiluminescent light employs an acid in an amount sufficient to produce an acidic pH. The acids that are effective include those compounds that are characterized by an acid ionization constant in water greater than $1 \times 10^{-8}$ as:
  a) carboxylic acids e.g. formic acid, acetic acid, propionic acid, chloroacetic acid, dichloroacetic acid, trichloroacetic acid, benzoic acid, nitrobenzoic acid, dinitrobenzoic acid, oxalic acid, malonic acid;
  b) phenols e.g.: dinitro-o-cresol, dinitrophenyl, picric acid;
  c) sulfonic acids: e.g. benzenesulfonic acid, methane-sulfonic acid, toluene-sulfonic acid;
  d) inorganic acids: e.g. phosphoric, hydrochlorid, sulfuric, nitric acid.

However, the presence of acid is not essential to obtain chemiluminescence.

The lifetime and the intensity of the chemiluminescent light can be regulated by the use of certain regulators such as:

1. By the addition of acid to the chemiluminescent composition to increase intensity and decrease lifetime, and by the addition of base to decrease intensity. Both the strength and the concentration of the base are critical for purposes of exactness in regulation.

2. By the variation of hydroperoxide. Both the type and the concentration of hydroperoxide are critical for the purposes of exactness in regulation.

The following examples are intended to illustrate the present invention and are in no way intended to limit the invention except at limited in the appended claims.

EXAMPLE I

Bis(1,2-dihydro-2-oxo-1-pyridyl)glyoxal

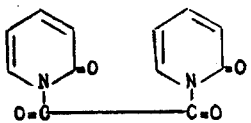

Preparation: (New compound)

(2-hydroxypyridine (4.76 g, 0.05 mole) dried by azeotropic distillation with benzene) is dissolved in 150 ml freshly distilled 1,2-dimethoxyethene. To the stirred solution 2,2 ml (0.025 mole) oxalyl-chloride and 5.05 g (0.05 mole) triethylamine are added. After 1 hour stirring the mixture is evaporated to dryness under vacuum and the residue is warmed with two 25 ml portions of chloroform to obtain 7.5g of white solid. The product is recrystallized from benzene to obtain 2.76 g (37.4%) of white crystals melting point 164° – 74°C.(d).

Analysis for $C_{12}H_8N_2O_4$:

| | C | | H | | N |
|---|---|---|---|---|---|
| calculated | 59.02 | calculated | 3.30 | calculated | 11.47 |
| found | 59.08 | found | 3.31 | found | 11.46 |

Infrared absorption bends in the $>c = o$ streching region taken in nujol: 1742, 1712, 1672 $cm^{-1}$.

EXAMPLE II

The tests of Table I were carried out as follows:
A. Approximately 3–5 mg. of the compound to be tested is added to a 5 ml. solution of about 1 mg. DPA and 0.2 ml anhydrous $H_2O_2$ in anhydrous 1,2-dimethoxyethane maintained at 25°C.
B. Approximately 3–5 mg. of the compound to be tested is added to a 5 ml slurry of 1 mg DPA, 0.2 g KOH (1 pellet) and 0.2 ml anhydrous $H_2O_2$ in anhydrous 1,2-dimethoxyethane maintained at 25°C.
C. As test A except that approximately 0.1 ml water is added prior to the addition of the compound being tested.
D. Approximately 3–5 mg of the compound to be tested is added to a 5 ml solution of 1 mg DPA and 0.2 ml $CH_3SO_3H$ in 1,2-dimethoxy-ethane containing 5% water and maintained at 25° C. About 0.5 ml 30% $H_2O_2$ is added immediately.

Qualitative intensities are based on the oxalyl chloride, hydrogen peroxide reaction taken as strong (S). Other designations are M = medium; W = weak; VW = very weak, barely visible.

Qualitative chemuliminescence tests of the compound are shown in Table I below.

TABLE I

| | Bis(1,2-dihydro-2-oxo-1-pyridyl)glyoxal Variable Reactants | | Evaluation Illumination | |
|---|---|---|---|---|
| Example No. | Peroxide | Other Reactants | Intensity | Lifetime |
| II A | Anhydrous $H_2O_2$ | | Medium | Long |
| II B | $H_2O_2$ | KOH | Weak | — |
| II C | $H_2O_2$ | $H_2O$ | Medium | Long |
| II D | $H_2O_2$ (30%) | $H_3O^+$ | Strong | Medium |

EXAMPLE III

Infrared Study of the Acid Catalyzed Rearrangement of Bis(1,2-dihydro-2-oxo-1-pyridyl)glyoxal to bis(-2-pyridyl)oxalate A stock solution of $5.8 \times 10^{-2}$ molar bis(1,2-dihydro-2-oxo-1-pyridyl)glyoxal in triethylphosphate is prepared, and the infrared spectrum of the solution is recorded from 1900 to 1500 $cm^{-1}$. To 0.75 ml aliquots of the stock solution, containing 10.7 mg ($4.3 \times 10^{-5}$ moles) of glyoxal, is added, respectively, 6$\mu$l ($8.6 \times 10^{-5}$ moles) of methanesulfonic acid, 1.6$\mu$l ($2.9 \times 10^{-5}$ moles) of phosphoric acid, and 7 $\mu$l ($8.6 \times 10^{-5}$ moles) of hydrochloric acid (37%), and the infrared spectra of the three solutions are recorded from 1900 to 1500 $cm^{-1}$ to determine if rearrangement takes place.

The results of the experiment show that the characteristic bands of the bis(1,2-dihydro-2-oxo-pyridyl)glyoxal at 1743, 1719, and 1680 $cm^{-1}$ in triethylphosphate solution are slowly diminished on the addition of acids, and the experiments reveal the appearance of a band at 1808 $cm^{-1}$ attributed to the formation of 2-pyridyl oxalate. The per cent conversion of N-acyl to 0-acyl compound was determined as: 30% in the case of methanesulfonic acid catalysis, and 5% in the cases both of phosphoric and hydrochloric acids after 5 min. elapsed time.

Both a study using I.R. spectroscopy of Example III and the strong chemiluminescence obtained in the presence of methane sulfonic acid in Table I of Example II points to the conclusion that bis(1,2-dihydro-2-oxo-1-pyridyl)glyoxal undergoes an acid catalyzed rearrangement to bis(2-pyridyl)oxalate prior to the chemiluminescent reaction. It is the latter compound which produces chemiluminescence in a reaction with $H_2O_2$ in the presence of a fluorescer.

EXAMPLE IV

The quantitative evaluation of the chemiluminescence of bis(1,2-dihydro-2-oxopyridyl)glyoxal shown in Table I is carried out as follows:
A. The reagents dissolved in dimethyl phthalate are mixed in a quartz cell provided with a magnetic stirrer. The order of mixing is as follows: glyoxal, 9,10-diphenyl anthracene, methane sulfonic acid, hydrogen peroxide. The reaction mixture then contains 0.001 mole $1^{-1}$ bis(1,2-dihydro-2-oxo-1-pyridyl)glyoxal, $6 \times 10^{-4}$ mole $1^{-1}$ 9.10-diphenyl anthracene $3.3 \times 10^{-4}$ mole $1^{-1}$ methane sulfonic acid and 0.1 mole $1^{-1}$ hydrogen peroxide. The emitted strong chemiluminescent light is measured by a radiometer-spectrophotometer at 25°C.

B. Part B is conducted the same way as experiment A, except that a higher, 0.01 mole $l^{-1}$ concentration of bis(1,2-dihydro-2-oxo-1-pyridyl)glyoxal is used.
C. Part C is conducted the same way as experiment B except that a higher, $3.3 \times 10^{-3}$ mole $l^{-1}$ concentration of methane sulfonic acid is used.
D. Part D is conducted the same way as experiment B except that 0.1 mole $l^{-1}$ phosphoric acid is used in the place of methane sulfonic acid.

EXAMPLE VI

The superior light producing capability of the bis(1,2-dihydro-2-oxo-1-pyridyl)glyoxal is demonstrated in Table IV.

All chemiluminescent measurements shown in Table IV are carried out by the use of a radiometer-spectrophotometer on a solution of 0.01 mole $l^{-1}$ of the chemiluminescent compound and $6 \times 10^{-4}$ mole $l^{-1}$ 9,10-diphenylanthracene at 25°C. The other reagents and solvent used vary as shown below:

TABLE II

The Effect of Acids on the Chemiluminescence Quantum Yield and Radiation Capacity of bis(1,2-dihydro-2-oxo-1-pyridyl)glyoxal yridyl)glyoxal in Dimethyl Phthalate Solution

| Ex. IV Part No. | Acid | glyoxal (mole $l^{-1}$) | acid concentration (mole $l^{-1} \times 10^4$) | mole ratio (acid to ester) | $t_{1/4} \, I_{max}$* (min.) | Quantum Yield (einstein mole$^{-1} \times 10^2$) | Radiation** Capacity (einstein $l^{-1} \times 10^4$) |
|---|---|---|---|---|---|---|---|
| A | Methane sulfonic | 0.0010 | 3.3 | 0.33 | 2.0 | 12.9 | 1.3 |
| B | Methane sulfonic | 0.0100 | 3.3 | 0.033 | 5.0 | 2.3 | 2.3 |
| C | Methane sulfonic | 0.0100 | 33.0 | 0.330 | <1.0 | 16.9 | 16.9 |
| D | Phosphoric (86%) | 0.0100 | 1000.0 | 10.00 | 4.0 | 2.1 | 2.1 |

*The time required for the light intensity to decrease to one quarter of its maximum value.
**Represents the ability of the chemiluminescent system to emit visible chemiluminescent light.

EXAMPLE V

The chemiluminescence of bis(1,2-dihydro-2-oxo-1-pyridyl)glyoxal is qualitatively studied in five solvents or solvent mixtures in the presence of three different fluorescers. The results are shown in Table III.

In Parts A and G of this Example, approximately 3–5 mg. of the compound to be tested is added to a 5 ml. solution of about 1 mg DPA and 0.2 ml anhydrous $H_2O_2$ in the indicated anhydrous solvent maintained at 25°C.

In Parts B and H of this Example, approximately 3–5 mg of the compound to be tested is added to a 5 ml slurry of 1 mg DPA, 0.2 g KOH (1 pellet) and 0.2 ml anhydrous $H_2O_2$ in the indicated anhydrous solvent maintained at 25°C.

Part C of this Example is carried out as test A, except that approximately 0.1 ml water is added prior to the addition of the compound being tested.

In Parts D, E and I of this Example, approximately 3–5 g of the compound to be tested is added to a 5 ml solution of 1 mg DPA and 0.2 ml $CH_3SO_3H$ in the indicated solvent maintaining at 25°C. About 0.2 ml 98% $H_2O_2$ is added immediately.

Part J is carried out as test A except 30% aqueous $H_2O_2$ is used.

Part L is carried out as test B, except 30% aqueous $H_2O_2$ is used.

Part K is carried out as test A, except 30% aqueous $H_2O_2$ is used.

Part M is carried out as test I, except 0.4 ml concentrated HCl is used in the place of methanesulfonic acid and 30% $H_2O_2$ is used in the place of 98% $H_2O_2$.

1. The experiments are carried out in dimethyl phthalate solution in the presence of varying amounts of hydrogen peroxide as follows:
   a. The hydrogen peroxide persent is 0.024 mole $l^{-1}$.
   b. The hydrogen peroxide present is 0.090 mole $l^{-1}$.
2. The experiment is carried out in dimethyl phthalate solution in the presence of 0.024 mole $l^{-1}$ hydrogen peroxide.
3. The experiment is carried out in dimethyl phthalate solution in the presence of varying amounts of hydrogen peroxide as follows:
   a. The hydrogen peroxide concentration is 0.024 mole $l^{-1}$.
   b. The hydrogen peroxide concentration is 0.09 mole $l^{-1}$.
   c. The hydrogen peroxide concentration is 0.09 mole $l^{-1}$, but $8.3 \times 10^{-4}$ mole $l^{-1}$ triethylamine is also present.
4. The experiment is carried out in triethyl phosphate solution in the presence of 0.018 mole $l^{-1}$ hydrogen peroxide.
5. 
   a. The experiment is carried out in dimethyl phthalate solution in the presence of 0.09 hydrogen peroxide.
   b. The experiment is carried out in 1,2-dimethoxyethane solution in the presence of 0.042 mole $l^{-1}$ hydrogen peroxide.
   c. The experiment is carried out in dimethyl adipate solution in the presence of 0.099 mole $l^{-1}$ hydrogen peroxide.
6. The experiment is carried out in dimethyl phthalate solution in the presence of 0.064 mole $l^{-1}$ hydrogen peroxide and 0.0037 mole $l^{-1}$ methane sulfonic acid.

TABLE III

| Ex. V Part | Bis(2-pyridyl)oxalate Evaluation Reaction Conditions | | | | | Results | |
|---|---|---|---|---|---|---|---|
| | Solvent | Fluorescer | Peroxide | Base | Acid | Intensity* | Lifetime |
| A | 1,2-dimethoxyethane (DME) | 9,10-diphenylanthracene (DPA) | anhydrous $H_2O_2$ | — | — | M | long |
| B | | | $H_2O_2$ | KOH | — | W | long |
| C | | | aqueous | — | — | M | long |

TABLE III-continued

| Ex. V Part | Bis(2-pyridyl)oxalate Evaluation Reaction Conditions | | | | | Results | |
|---|---|---|---|---|---|---|---|
| | Solvent | Fluorescer | Peroxide | Base | Acid | Intensity* | Lifetime |
| D | | | $H_2O_2$ | — | $H_3O^{+***}$ | VW | Medium |
| E | | Rubrene | $H_2O_2$ | — | $H_3O^+$ | VW | Fast |
| F | DME/$H_2O$(1:1) | DPA | $H_2O_2$ aqueous | KOH | — | None | — |
| G | dimethyl-phthalate | DPA | 30% $H_2O_2$ anhydrous | — | — | M – W | long |
| H | | DPA | $H_2O_2$ | KOH | — | W | long |
| I | | DPA | $H_2O_2$ | —$H_3O^+$ | S | fast | |
| J | acetic acid | DPA | 30% $H_2O_2$ | — | — | S | long |
| K | | disodium fluorescein | 30% $H_2O_2$ | — | — | None | — |
| L | water | | 30% $H_2O_2$ | KOH | — | None | — |
| M | | N-methyl-acridinium chloride | 30% $H_2O_2$ | —HCl | None | — | |

*Qualitative intensities are based on the oxalyl chloride, hydrogen peroxide reaction taken as strong [S]. Other designations are M = medium; W = weak; VW = very weak, barely visible.
**Acetic acid was used in the place of methane sulfonic acid.

TABLE IV

| No. | Chemiluminescent Compound | Summary of High Radiation Capacities | | | |
|---|---|---|---|---|---|
| | | Solvent* | Hydrogen-Peroxide (mole $l^{-1}$) | Radiation Capacity** (einstein $l^{-1} \times 10^2$) | $t_{1/4} \, I_{max}$*** |
| 1 | Bis(2,4-dinitrophenyl)oxalate | | | | |
| | a) | DMP | 0.024 | 8.5 | 3 |
| | b) | DMP | 0.090 | 8.1 | 12 |
| 2 | Bis(2,4-dinitro-6-methylphenyl) oxalate | DMP | 0.024 | 7.1 | 2 |
| 3 | Bis(2-formyl-2-nitrophenyl)oxalate | | | | |
| | (a) | DMP | 0.024 | 8.7 | 89 |
| | b) | DMP | 0.090 | 8.0 | 75 |
| | c) | DMP | $0.090^a$ | 7.0 | 20 |
| 4 | Bis(3-trifluoromethylphenyl)oxalate | TEP | 0.018 | 7.2 | 26 |
| 5 | Bis(pentafluorophenyl)oxalate | | | | |
| | a) | DMP | 0.090 | 7.6 | 58 |
| | b) | DME | 0.042 | 9.7 | 6 |
| | c) | DMA | 0.099 | 8.1 | 20 |
| 6 | Bis(1,2-dihydro-2-oxo-1-pyridyl) glyoxal | DMP | 0.064 | 16.9 | <1 |

*DMP is dimethyl phthalate, DME is 1,2-dimethoxyethane, DMA is dimethyl adipate, TEP is triethyl phosphate.
**Time required for the light intensity to decrease to 1/4 of its maximum value.
***Represents the ability of the chemiluminescent system to emit chemiluminescent light.

EXAMPLE VII

The preparation of bis(5-oxo-1,5-dihydro-1-quinol)-glyoxal is carried out the same way as that described in Example I for bis(1,2-dihydro-2-oxo-1-pyridyl)glyoxal except 5-hydroxy quinoline is used in the place of 2-hydroxy pyridine.

It is within the scope of this invention to make such modifications of the compositions and processes disclosed herein as would be obvious to a person of ordinary skill in this art, and it is to be understood that the examples illustrating this invention are intended to limit the invention only insofar as is stated in the specification and as the following claims are limited. Also, it is within the scope of this invention to form an apparatus or article such as a container which, for example, may be either (1) a substantially insoluble or alternatively (2) a dissolvable capsule in which the reactant or composition of this invention is substantially enclosed for subsequent reaction with other ingredients necessary to produce chemiluminescent light.

EXAMPLE VIII

Bis(1,2-dihydro-2-oxo-1-pyridyl)glyoxal is tested for chemiluminescence in a reaction with hydroperoxides other than hydrogen peroxide. The tests carried out are as follows:

A. Approximately 3 mg glyoxal is added to a 5 ml solution of 1 mg DPA and 25 mg peroxy-4-nitrobenzoic acid in 1,2-dimethoxyethane (DME) maintained at about 25%. No substantial chemiluminescence is observed.

B. Test is similar to test A except 0.2 g KOH is also added. No. substantial chemiluminescence is observed.

C. Test is similar to test A except 0.1 ml water is also added. No substantial chemiluminescence is observed.

D. Test is similar to test A except 0.1 ml methanesulfonic acid is also added. Medium weak chemiluminescence is observed.

EXAMPLE IX

Tests described in Example VIII are repeated but t-butylhydroperoxide is used in the place of peroxy-4-nitro benzoic acid. The results of the tests are as follows:

A. No substantial chemiluminescence is observed.
B. No substantial chemiluminescence is observed.
C. No substantial chemiluminescence is observed.
D. Medium chemiluminescence is observed.

I claim:
1. Bis(1,2-dihydro-2-oxo-1-pyridyl)glyoxal.

* * * * *